United States Patent [19]

Lippa

[11] Patent Number: 4,777,128
[45] Date of Patent: Oct. 11, 1988

[54] FLUORESCENCE IMMUNOASSAY INVOLVING ENERGY TRANSFER BETWEEN TWO FLUOROPHORES

[75] Inventor: Arnold S. Lippa, Franklin Lakes, N.J.

[73] Assignee: Ethigen Corporation, Los Angeles, Calif.

[21] Appl. No.: 866,952

[22] Filed: May 27, 1986

[51] Int. Cl.[4] .................. G01N 33/533; G01N 33/542
[52] U.S. Cl. ......................................... 435/5; 436/500; 436/501; 436/537; 436/800; 530/391
[58] Field of Search ............... 436/536, 501, 537, 800, 436/500; 435/5; 530/391

[56] References Cited

U.S. PATENT DOCUMENTS

| | | | |
|---|---|---|---|
| 3,996,345 | 12/1976 | Ullman et al. | 424/12 |
| 4,133,873 | 1/1979 | Noller | 424/8 |
| 4,174,384 | 11/1979 | Ullman et al. | 424/8 |
| 4,199,559 | 4/1980 | Ullman et al. | 424/8 |
| 4,233,402 | 11/1980 | Maggio et al. | 424/7 |
| 4,238,195 | 12/1980 | Boguslaski et al. | 23/230 B |
| 4,261,968 | 4/1981 | Ullman et al. | 424/8 |
| 4,272,505 | 6/1981 | Smith | 424/8 |
| 4,318,707 | 3/1982 | Litman et al. | 23/230 B |
| 4,318,846 | 3/1982 | Khanna et al. | 260/112 B |
| 4,385,126 | 5/1983 | Chen et al. | 436/518 |
| 4,407,964 | 10/1983 | Elings et al. | 436/518 |
| 4,499,052 | 2/1985 | Fulwyler | 436/172 |
| 4,536,479 | 8/1985 | Vander-Mallie | 436/537 |
| 4,542,104 | 9/1985 | Stryer et al. | 436/800 |
| 4,666,862 | 5/1987 | Chan | 436/537 |

*Primary Examiner*—Esther M. Kepplinger
*Assistant Examiner*—David A. Saunders
*Attorney, Agent, or Firm*—Bernard, Rothwell & Brown

[57] ABSTRACT

In a fluorescence immunoassay system, first and second fluorophores are covalently bound to one of a member of a specific binding pair of liquid and receptor, the first of said fluorophores being capable of absorbing light at a first wavelength to produce light emission at a second wavelength, which second wavelength can be absorbed by the second fluorophore.

44 Claims, 4 Drawing Sheets

FLUORESCENCE IMMUNOASSAY INVOLVING ENERGY TRANSFER BETWEEN TWO FLUOROPHORES

BACKGROUND OF THE INVENTION

1. Field of the Invention

The present invention relates to the field of fluorescence immunoassays useful in the determination of analytes in fluid samples.

2. Description of the Background Art

There are several known methods for detecting analytes (e.g., hormones, enzymes, other proteins, therapeutic agents, drugs of abuse, etc.) in liquid samples such as biological fluids. Among the known types of methods, immunoassays have emerged as sensitive techniques for determining minute amounts of certain organic compounds. Immunoassay methods generally are based on the ability of a receptor molecule, usually an antibody, to specifically recognize a particular spatial and/or polar organization of a ligand molecule, and thereby selectively bind to the ligand molecule.

Certain of the known immunoassay techniques involve the use of fluorophore molecules, which are able to absorb light a one wavelength and emit light at another wavelength. For example, U.S. Pat. No. 4,272,505 to Smith describes a method for assaying a biological fluid sample for a thyroid hormone. This method is based on the principle of fluorescence suppression of a fluorophore by thyroid hormone. The Smith method is a competitive-type assay involving formation of a mixture of a fluid sample with a known amount of fluorophore-labeled thyroid hormone, the fluorophore having a fluorescence level which is substantially suppressed by the thyroid hormone to which the fluorophore is bound. Antibody capable of binding to the fluorophore-labeled thyroid hormone as well as thyroid hormone present in the sample is introduced into the mixture. The antibody is thought to sterically alter the labeled thyroid hormone, thus changing the degree of suppression of the fluorescence of the fluorophore bound thereto. The fluorescence level of the mixture then is measured and the amount of thyroid hormone in the sample is calculated by comparing the fluorescence level of the mixture with a standard fluorescence level.

U.S. Pat. No. 4,133,873 to Noller discloses a method for determining the amount of a member of a group consisting of an extracellular antigen and an extracellular antibody capable of specifically combining with said antigen. The method involves tagging the member with a fluorophore and exposing the tagged member to a pulse of light of a first wavelength sufficient to cause emission by the tagged exposed member of secondary light having a second wavelength different from the first wavelength. The secondary light is sensed to generate a perceptible signal in response to and commensurate with the sensed secondary light.

An immunoassay utilizing two different ligands tagged with separate fluorophores which independently fluoresce at different wavelengths is disclosed in U.S. Pat. No. 4,385,126 to Chen et al. The two tagged ligands are capable of immunologically binding to each other, and the two different ligands may be detected independently through their independent tagging constituents (fluorophores) for quality control, internal calibration (standardization), determination of viability and shelf life, and the like.

U.S. Pat. Nos. 3,996,345, 4,174,384, 4,199,559 and 4,261,968, all to Ullman et al., disclose immunoassays employing antibodies and a fluorescer-quencher chromophoric pair. The methods are based on the phenomenon of energy transfer between two chromophores which form a fluorescer-quencher pair. The methods involve irradiation of a fluorescer molecule with light of a first wavelength which is absorbed by the fluorescer and resultant emission of light of a longer wavelength by the fluorescer. If a quencher chromophore is within less than about 100 Å of the fluorescer and absorbs light at the wavelength of emission of the fluorescer, the fluorescer will transfer to the quencher chromophore the energy which would otherwise have been emitted as light. The Ullman methods all involve measurement of the decrease of fluorescence (light emission) of the fluorescer chromophore resulting from energy transfer to the quencher chromophore. Ligand and antiligand can be separately labeled with fluorescer and quencher, or one group of antibodies can be labeled with fluorescer and another group of antibodies labeled with quencher for detection of ligand capable of immunologically binding to more than one antibody.

U.S. Pat. No. 4,536,479 to Vander-Mallie discloses an immunoassay method for the detection of an analyte in a test sample wherein a reaction mixture is formed between test sample and a pair of reagents. The first reagent is an idiotypic anti-analyte antibody labeled with a first fluorophore. The second reagent is an anti-idiotypic antibody labeled with a second fluorophore, which anti-idiotypic antibody is capable of competing with analyte in the sample for the idiotypic anti-analyte antibody. One of the fluorophores is capable of absorbing incident light at a first wavelength to produce light emission at a second wavelength which second wavelength can be absorbed by the other fluorophore to produce emission at a third wavelength. For the detection of analyte in the reaction mixture, the reaction mixture is irradiated with incident light of the first wavelength, and the intensity of light of the second or third wavelength is measured, which intensity is related to the amount of analyte initially present in the test sample.

All of the known fluorescence immunoassay methods have disadvantages and limitations, leaving a continuing need for new, rapid and sensitive methods for detecting analytes in fluid samples.

SUMMARY OF THE INVENTION

In accordance with the present invention, a member of a specific binding pair of ligand and receptor is provided, the member being covalently bound to first and second fluorophores. The first of the fluorophores is capable of absorbing light at a first wavelength to produce light emission at a second wavelength, which second wavelength can be absorbed by the second fluorophore. The method of the invention utilizes a member of a specific binding pair as defined above in the determination of the presence or amount of the other member of the specific binding pair in a fluid sample.

DESCRIPTION OF THE PREFERRED EMBODIMENTS

Figure 1:
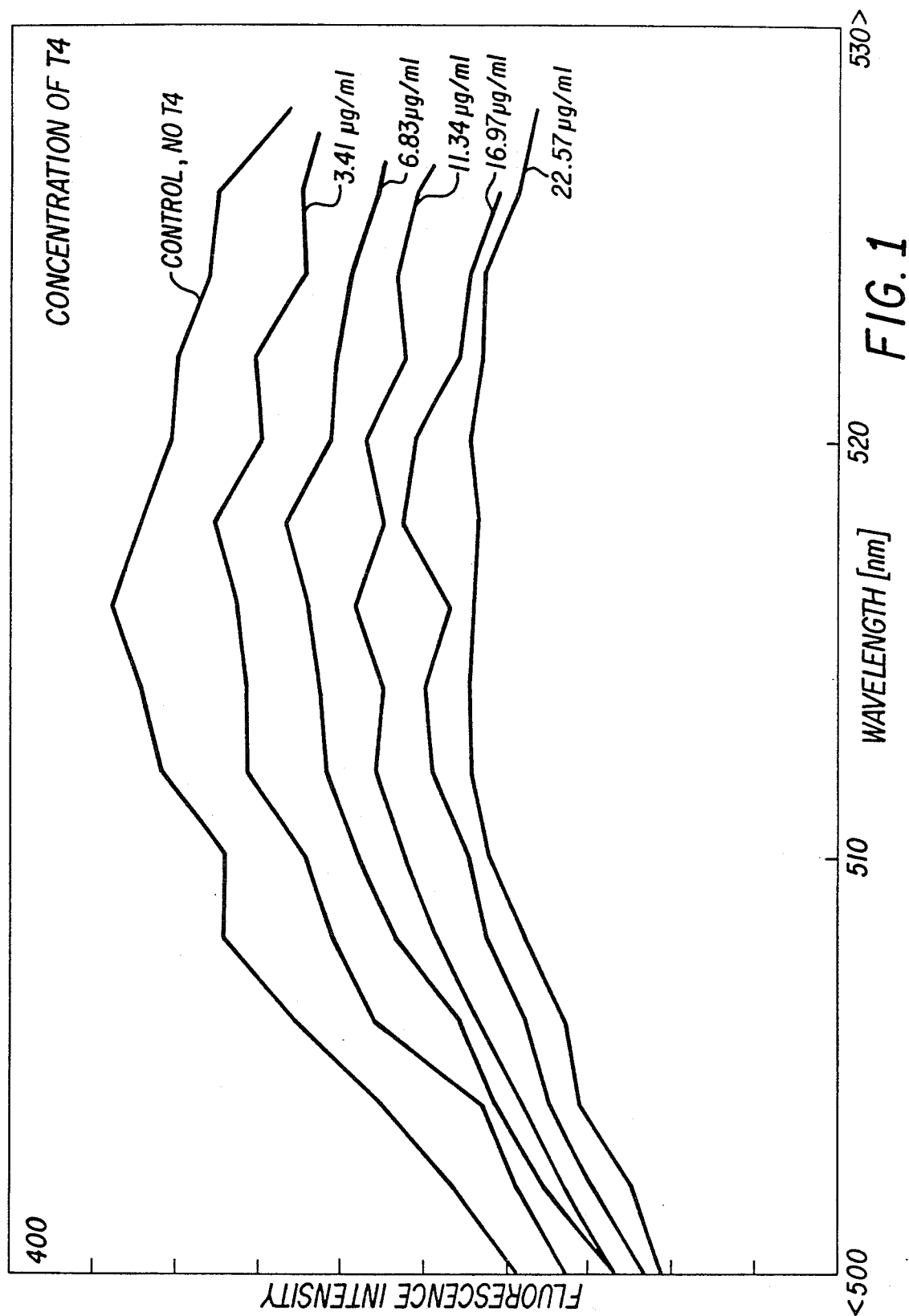
FIG. 1 is a graphic depiction showing reduction of fluorescence excitation transfer between fluorescein and eosin bound to anti-thyroxine (anti-T4) in the presence of varying concentrations of thyroxine (T4).

In carrying out an immunoassay in accordance with the present invention, a member of a specific binding pair of ligand and receptor is employed, which member is covalently bound to first and second fluorophores. The first and second fluorophores can be covalently bound to either the ligand or receptor member of the specific binding pair for detection of the other member of the specific binding pair.

Ligand refers to an organic molecule or assemblage with at least one functionality having a particular spatial and/or polar organization for which a receptor is either naturally available or can be prepared.

Receptor refers to a molecule which is capable of specifically recognizing a certain functionality of a ligand molecule having a particular spatial and/or polar organization, and thereby selectively binding to the ligand molecule. Receptors generally are antibodies although enzymes, proteins, nucleic acids, and certain globulins, may also act as receptors.

A fluorophore is a molecule capable of absorbing light at one wavelength and emitting light at another wavelength.

In accordance with the invention, the first and second fluorophores covalently bound to ligand or receptor are members of a fluorescence energy transfer system pair where the emission spectrum of the first fluorophore overlaps well with the excitation spectrum of the other fluorophore such that when the first and second fluorophores interact by fluorescence energy transfer, the fluorescence of the first fluorophore is absorbed by the second fluorophore by energy transfer.

Examples of fluorophores having overlapping emission and excitation spectrums include fluorescein (excitation λ495 nm, emission λ520 nm), eosin (excitation λ520 nm, emission λ545 nm), fluorescamine (excitation λ390 nm, emission λ520 nm), and tetramethyl rhodamine (excitation 520 nm, emission λ550 nm).

According to one embodiment, the fluorescence energy transfer system pair includes fluorescein as a first fluorophore and eosin as a second fluorophore.

In accordance with one embodiment, first and second fluorophores are brought within excitation transfer proximity by covalently binding both chromophores to one member of a specific binding pair of ligand and receptor.

The first and second fluorophores are covalently bound to ligand or receptor in sufficiently close proximity to each other (generally less than about 100 Å) such that an energy transfer from the first fluorophore to the second fluorophore will take place upon excitation of the first fluorophore by light of a first (excitation) wavelength. Alternatively, the bound fluorophores are proximally positioned by binding of ligand and receptor.

The non-covalent attachment of the fluorophore-labeled member of the specific binding pair to the unlabeled member may either interfere with or enhance the fluorescence excitation transfer resulting in either a quenching or enhancement of fluorescence of one or both fluorophores.

The fluorophores can be covalently bound to ligand or receptor using any suitable method known in the art. For example, if receptor is antibody, the first and second fluorophores generally are sequentially bound to the antibody. Antibodies generally have a number of active amino groups which can be used for covalently binding fluorophores to the antibody. Conveniently, a fluorophore can have a non-oxocarbonyl functionality (including the nitrogen and sulfur analogs thereof) or active α-halocarbonyl functionality. Illustrative functionalities for linking a fluorophore to antibody include acylhalides, mixed anhydrides, imidate alkyl esters, isothiocynate, chlorobromo- or iodoacetyl, and the like.

The conditions for covalent bonding employ moderate temperatures, e.g., 0°–40° C., in aqueous media at moderate pH. Covalent bonding of fluorophores to protein is known in the art, see, e.g., The et al., *Immunology*, 18:865 (1970); Cebra et al., *J. Immunol.*, 95:230 (1965); Goldman, *Fluoroescence Antibody Methods*, Academic Press, New York (1968). Energy transfer between a fluorescence energy donor (such as fluorescein) in a suitable energy acceptor (such as eosin) depends on the inverse sixth power of the distance between donor and acceptor as well as the dielectric constant of the immediate environment. Energy transfer is generally most efficient over a distance on the order of 40–50 Å, such that a fluorescence energy donor transfers energy to a nearest adjacent acceptor rather than a more distant one.

The invention will further be specifically described with respect to the first and second fluorophores covalently bound to receptor (antibody) although it is to be understood that the invention is equally applicable to ligand-bound fluorophore pairs.

With first and second fluorophores proximally bound to antibody absorption of light by the first fluorophore at a first excitation wavelength ($\lambda_{ex1}$) produces light emission at a second emission wavelength ($\lambda_{em1}$), and the second wavelength ($\lambda_{em1}$) can be absorbed by the second fluorophore to produce an emission at a third wavelength ($\lambda_{em2}$).

Binding of labeled antibody to ligand inhibits energy transfer from the first fluorophore to the second fluorophore, and thus increases fluorescence of the first fluorophore (i.e., increases emission of light wavelength $\lambda_{em1}$), and correspondingly decreases fluorescence of the second fluorophore (i.e., emission of light wavelength $\lambda_{em2}$) due to the inhibition of energy transfer between the first fluorophore and the second fluorophore by the bound ligand molecule.

Fluorophore-labeled antibody to ligand is utilized to determine the presence or amount of ligand in a fluid sample. A reaction mixture is formed by contacting the fluid sample with double fluorophore-labeled antibody, and specific binding of labeled antibody and unlabeled ligand inhibits absorption by the second fluorophore of light emitted by the first fluorophore.

Inhibition of energy transfer between the first and second fluorophores upon irradiation of the reaction mixture with light of a first excitation wavelength ($\lambda_{ex1}$) is a function of the amount of unlabeled analyte (unlabeled ligand) present in the fluid sample. The quantity of unlabeled ligand can be determined by irradiating the reaction mixture with light of a first excitation wavelength ($\lambda_{ex1}$) and measuring the amount of fluorescence from the reaction mixture of light of wavelength $\lambda_{em1}$ or $\lambda_{em2}$, which fluorescence is directly related to the amount of analyte (unlabeled ligand) present in the fluid sample.

The method of the present invention can be carried out either by measuring the increase of $\lambda_{em1}$ emission due to receptor-ligand binding as compared to a standard containing labeled antibody in the absence of ligand, or measuring the decrease in $\lambda_{em2}$ emission as a result of antibody/ligand binding as compared to a standard containing like amount of labeled antibody in the absence of ligand.

The exact mechanism of the excitation energy transfer changes brought about by binding of ligand and antibody is not known, and may be due to differing factors depending upon the ligand/receptor pair used. Without being bound to any particular theory, such mechanisms may include steric or physical hinderance by the bound ligand of energy transfer between the first and second fluorophores, or other changes in the microenvironment of the bound ligand/receptor pair causing an emission change.

Non-limiting examples of ligand/receptor pairs with which the invention has heretofore been practiced include hepatitis B surface antigen and antibody thereto, immunoglobulin G and antibody thereto, thyroxine and antibody thereto, and digoxin and antibody thereto.

The present invention provides a specific and sensitive non-competitive immunoassay having the benefits of simplicity and requiring fewer steps than prior art assays. The immunoassay of this invention is also more economical than prior art assays, requiring fewer reagents.

The invention is further illustrated by the following examples which are not intended to be limiting.

EXAMPLE I

Thyroxine (T4) Assay

1. Preparation of Fluorescein Labeled T4 Antibody (T4 AB)

Fluorescein labeled T4 AB was obtained by reaction of 1 volume of 20 g/l of fluorescein isothiocynate (FTIC) with 2 volumes of 20 g/l T4 AB (Calbiochem-Behring) in a pyridine/water/triethyl-amine medium of composition 9:1.5:0.1 v/v/v. Reaction was complete after 1 hour at room temperature. The excess of unreacted fluorescein was removed by dialysis against 5 mM K-phosphate buffer pH 7.35 containing 150 mM NaCl. Overnight dialysis was sufficient to remove unreacted material.

2. Preparation of Double Labeled T4 AB

Eosin-maleimide was obtained from Molecular Probes, Inc. Double-labeled T4 AB was prepared by incubating fluorosceine-labeled T4 AB with eosin maleimide (20×molar excess) in 20 mM histidine-HCl buffer (pH 7.40) for 3 hours at 20°-25° C. The excess of unreacted eosin was removed by dialysis against 5 mM K-phosphate buffer pH 7.35 containing 150 mM NaCl. Five changes of the dialysate was found to be enough to remove the unreacted material. The determination of the concentration of bound eosin was obtained by measuring the optical density at 528 nm using an extinction coefficient of 70,000/M cm.

3. Reaction of Thyroxine (T4) with Double-Labeled T4 Antibody

The reaction of antigen with double-labeled antibody took place in 2 mL of a 5 mM sodium phosphate buffer containing 0.15 M NaCl (pH 8.0) inside a spectrophotometric cell (cuvette) after 1–2 minutes of incubation at room temperature.

4. Results

Figure 2:
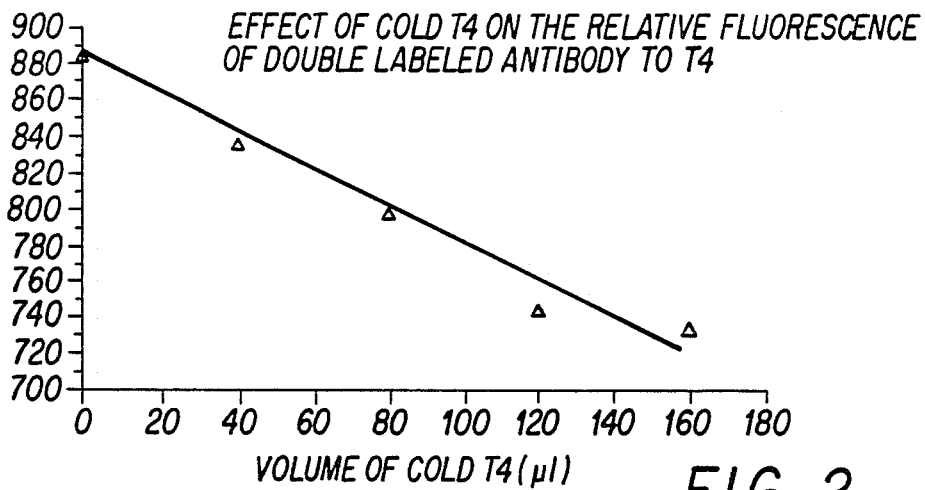
FIG. 2 is a graphic depiction showing the effect of cold T4 on the relative fluorescence of double-labeled antibody to T4.

As can be seen in FIG. 1, the presence of thyroxine reduced the fluorescence excitation transfer between the two chromophores. FIG. 2 demonstrates that increasing volumes of a 1 mg/ml concentration of thyroxine produced a concentration dependent decrease of the relative fluorescence of the double-labeled antibody when measured at peak fluorescent intensity. At the concentrations used, this assay was linear. No significant changes in fluorescence were observed with equal volumes of vehicle solution or BSA (1 mg/ml).

EXAMPLE II

Assay for Hepatitis B Surface Antigen (HBsA)

1. Preparation of Double Labeled Antibody to HBsA

Material was obtained from Nuclear Medicine Laboratories in a kit form (NML*HBsAg RIA). Fluorescein and eosin labeling of the antibody to HBsA was accomplished using essentially the same methods set forth in Example I for the T4 assay.

2. Reaction of HBsA to Anti-HBsA

The reaction of antigen with double-labeled antibody took place in 2 mL of a 5 mM sodium phosphate buffer containing 0.15 M NaCl (pH 8.0) inside a spectrophotometric cell (cuvette) after 1–2 minutes of incubation at room temperature.

3. Results

Figure 3:
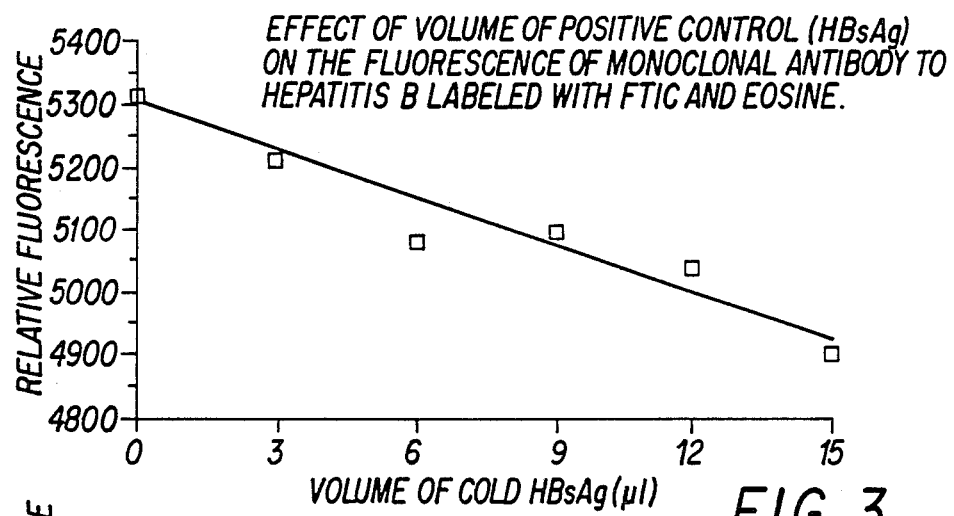
FIG. 3 is a graphic depiction showing the effect of volume of Hepatitis B Surface Antigen on the fluorescence of monoclonal antibody to Hepatitis B labeled with fluorescein isothiocynate and eosin.

As can be seen in FIG. 3, increasing amounts of HBsA produced a concentration dependent decrease of the relative fluorescence of double-labeled antibody to HBsA when measured at peak fluorescence intensity.

EXAMPLE III

Immunoglobulin G (IgG) Assay

1. Preparation of Double-Labeled Antibody to IgG

The materials were obtained commercially and labeling was performed essentially as described in Example I for the T4 assay.

2. Reaction of IgG to Anti-IgG

The reaction of antigen with double-labeled antibody took place in 2 mL of a 5 mM sodium phosphate buffer containing 0.15 M NaCl (pH 8.0) inside a spectrophotometric cell (cuvette) after 1–2 minutes of incubation at room temperature.

3. Results

Figure 4:
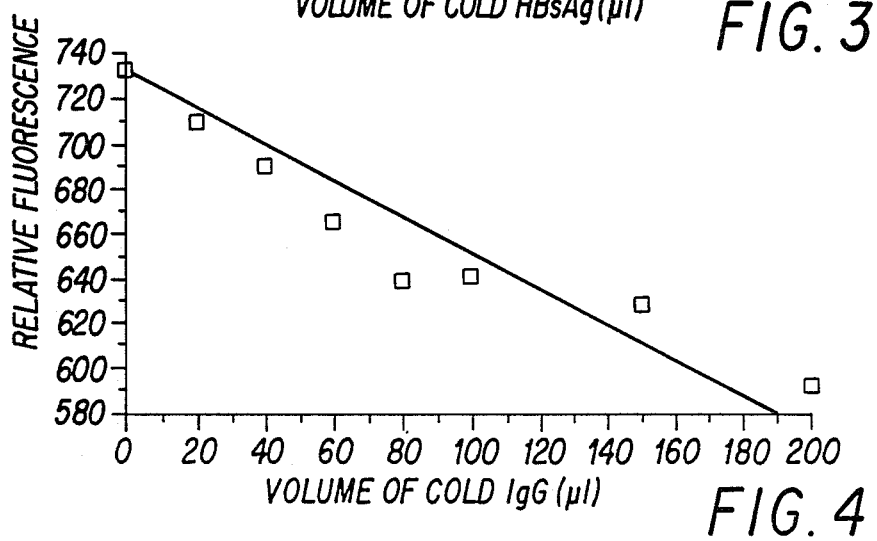
FIG. 4 is a graphic depiction showing the effect of volume of immunoglobulin G (IgG) on the fluorescence of antibody to IgG labeled with fluorescein isothiocynate and eosin.

In a manner similar to that observed in the two prior assays, increasing amounts of IgG decreased the relative fluorescence of the double-labeled antibody when measured at peak fluorescence intensity (see FIG. 4).

EXAMPLE IV

Digoxin Assay

1. Preparation of Double-Labeled Digoxin Antibody

The materials were obtained commercially and digoxin antibody was double-labeled essentially as described in Example I for the T4 assay.

2. Reaction of Digoxin to Anti-Digoxin

The reaction of antigen with double-labeled antibody took place in 2 mL of a 5 mM sodium phosphate buffer containing 0.15 M NaCl (pH 8.0) inside a spectrophotometric cell (cuvette) after 1-2 minutes of incubation at room temperature.

3. Results

Figure 5:
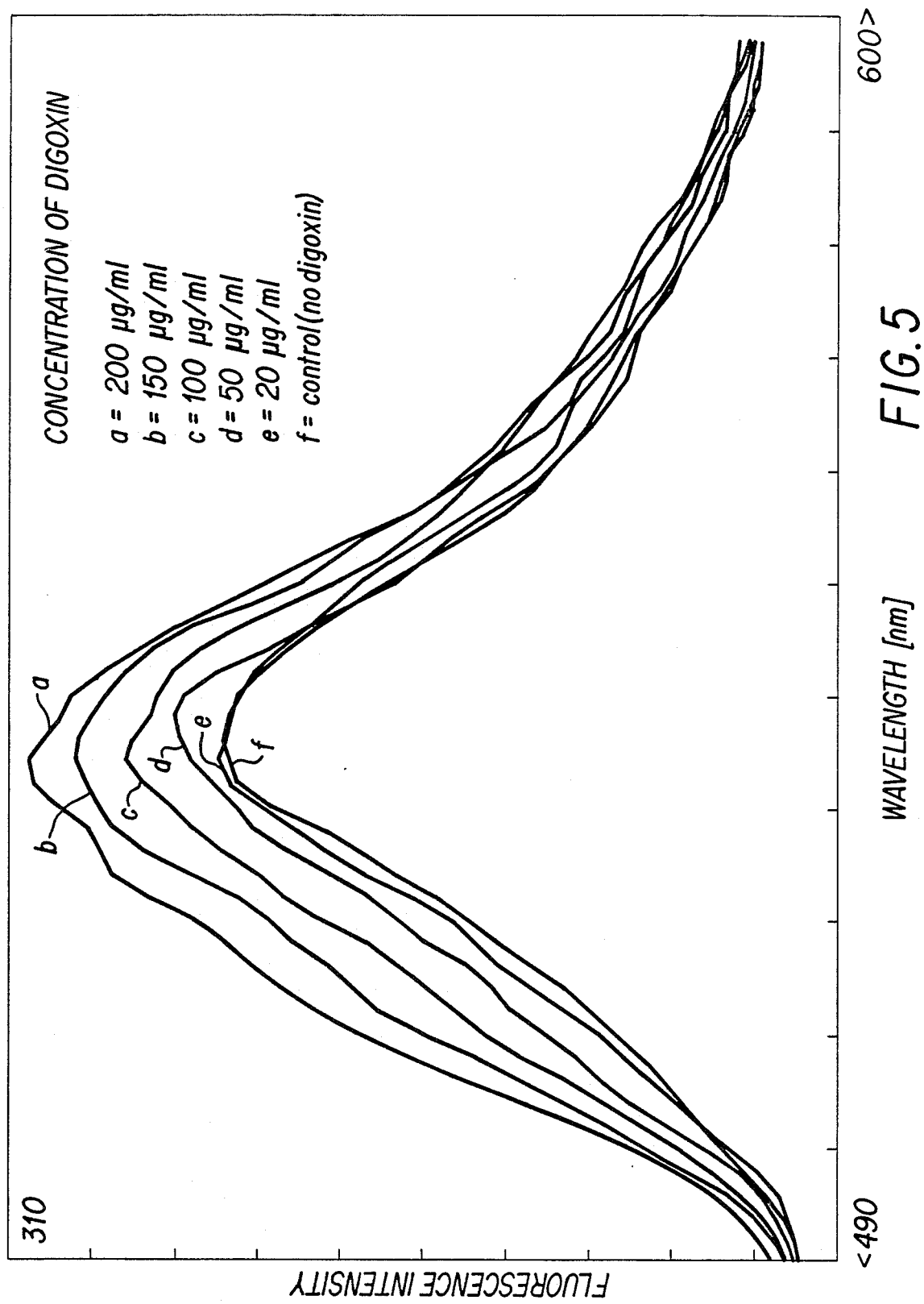
FIG. 5 is a graphic depiction showing an increase in fluorescence excitation transfer upon incubation of double-labeled digoxin antibody (anti-DG) with varying concentrations of digoxin (DG).
Figure 6:
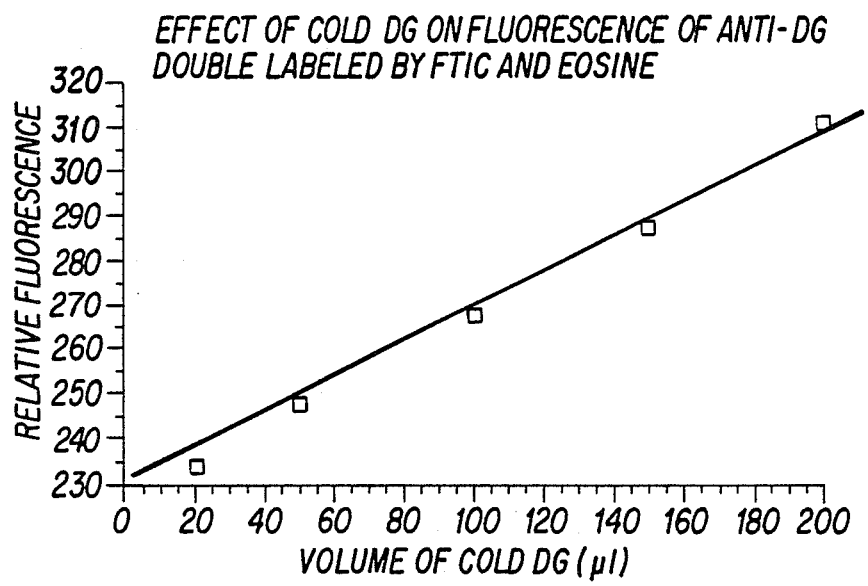
FIG. 6 is a graphic depiction showing the effect of cold DG n the fluorescence of anti-DG double labeled by fluorescein isothiocynate (FTIC) and eosin.

Unlike the above assays, incubation of double-labeled digoxin antibody with digoxin increased the fluorescence excitation transfer (see FIG. 5). As can be seen in FIG. 6, increasing amounts of digoxin produced a concentration dependent increase in relative fluorescence when measured at peak fluorescence intensity.

EXAMPLE V

IgG Measurement in Human Serum

Figure 7:
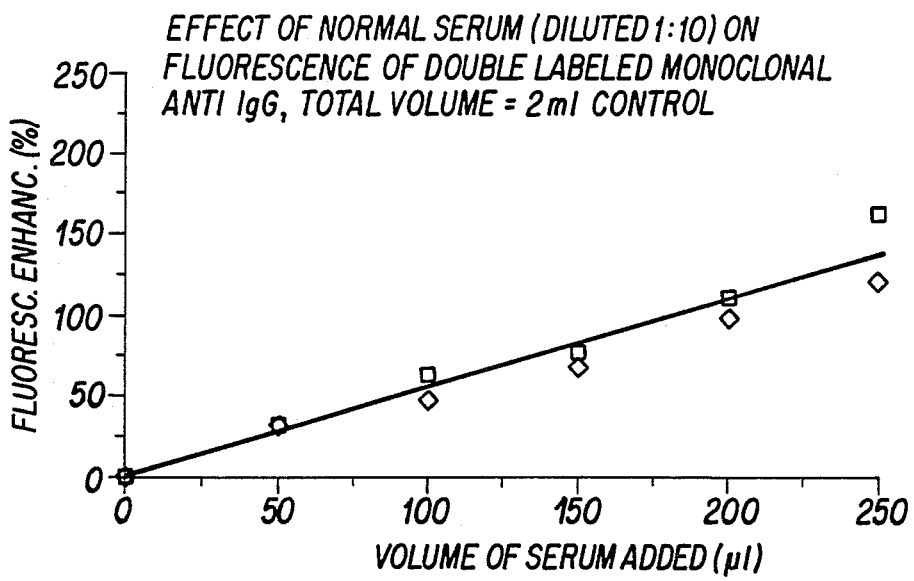
FIG. 7 is a graphic depiction showing the effect of normal serum (diluted 1:10) on fluorescence of double-labeled monoclonal anti-IgG.

IgG was measured in human serum by combining a small volume of serum (50-250 μl) with a detergent (e.g., sodium dodecylsulfate (SDS)) so that the final concentration of the SDS was about 10%. This mixture was added to 5 mM sodium phosphate buffer containing 0.15 M NaCl (pH 8.0) inside a spectrophotometric cell (cuvette) after 1-2 minutes of incubation at room temperature, and the assay completed as described in Example I. A graph displaying the ability to measure IgG in human serum samples is depicted in FIG. 7.

What is claimed is:

1. A member of a specific binding pair of ligand and receptor, said member being covalently bound to first and second fluorophores, the first of said fluorophores being capable of absorbing light energy at a first wavelength to produce light energy emission at a second wavelength, which second wavelength can be absorbed by the second fluorophore, wherein specific binding of ligand and receptor affects energy transfer between said fluorophores.

2. The member of claim 1 wherein specific binding of the pair inhibits absorption by the second fluorophore of light emitted by the first fluorophore.

3. The member of claim 1 wherein specific binding of the pair enhances absorption by the second fluorophore of light, emitted by the first fluorophore.

4. The member of claim 1 wherein said member is receptor and said receptor is antibody to said ligand.

5. The member of claim 4 wherein the first fluorophore is fluorescein and the second fluorophore is eosin.

6. The member of claim 4 wherein said ligand is Hepatitis B Surface Antigen, Immunoglobulin, Thyroxin or Digoxin.

7. The member of claim 1 wherein the second fluorsphore produces an emission of light at a third wavelength upon absorbing light of the second wavelength.

8. The member of claim 7 wherein said member is receptor and said receptor is antibody to said ligand.

9. The member of claim 8 wherein the first fluorophore is fluorescein and the second fluorophore is eosin.

10. The member of claim 8 wherein said ligand is Hepatitis B Surface Antigen, Immunoglobulin G, Thyroxin or Digoxin.

11. The member of claim 7, wherein specific binding of the pair inhibits absorption by the second fluorophore of light emitted by the first fluorophore.

12. The member of claim 11 wherein said member is receptor and said receptor is antibody to said ligand and said ligand is Digoxin.

13. The member of claim 11 wherein said member is receptor and said receptor is antibody to said ligand.

14. The member of claim 13 wherein said ligand is Digoxin.

15. The member of claim 11 wherein the first fluorophore is fluorescein and the second fluorophore is eosin.

16. The member of claim 15 wherein said member is receptor and said receptor is antibody to said ligand and said ligand is Digoxin.

17. The member of claim 7 wherein specific binding of the pair enhances absorption by the second fluorophore of light emitted by the first fluorophore.

18. The member of claim 17 wherein said member is receptor and said receptor is antibody to said ligand and said ligand is Hepatitis B Surface Antigen, Immunoglobulin G, or Thyroxin.

19. The member of claim 17 wherein said member is receptor and said receptor is antibody to said ligand.

20. The member of claim 19 wherein said ligand is Hepatitis B Surface Antigen, Immunoglobulin G, or Thyroxin.

21. The member of claim 17 wherein the first fluorophore is fluorescein and the second fluorophore is eosin.

22. The member of claim 21 wherein said member is receptor and said receptor is antibody to said ligand and said ligand is Hepatitis B Surface Antigen, Imunoglobulin G, or Thyroxin.

23. A method for determining the presence or amount of a first member of a specific binding pair of ligand and receptor in a fluid sample, the method comprising:
  (a) forming a reaction mixture of contacting said sample with a second member of said pair, said second member being covalently bound to first and second fluorophores, the first of said fluorophores being capable of absorbing light at a first wavelength to produce light emission at a second wavelength, which second wavelength can be absorbed by the second fluorophore, wherein specific binding of ligand and receptor affects energy transfer between said fluorophores;
  (b) irradiating the reaction mixture with light of the first wavelength; and
  (c) measuring the amount of fluorescence from one of said fluorophores in the reaction mixture as compared to a standard.

24. The method of claim 23 wherein specific binding of the pair inhibits absorption by the second fluorophore of light emitted by the first fluorophore.

25. The method of claim 23 wherein specific binding of the pair enhances absorption by the second fluorophore of light emitted by the first fluorophore.

26. The method of claim 23 wherein said second member is receptor and said receptor is antibody to said ligand.

27. The method of claim 26 wherein the first fluorophore is fluorescein and the second fluorophore is eosin.

28. The method of claim 26 wherein said ligand is Hepatitis B Surface Antigen, Immunoglobulin G, Thyroxin or Digoxin.

29. The method of claim 23 wherein the second fluorophore produces an emission of light at a third wavelength upon absorbing light of the second wavelength.

30. The method of claim 29 wherein said second member is receptor and said receptor is antibody to said ligand.

31. The method of claim 30 wherein the first fluorophore is fluorescein and the second fluorophore is eosin.

32. The method of claim 30 wherein said ligand is Hepatitis B Surface Antigen, Immunoglobulin G, Thyroxin or Digoxin.

33. The method of claim 29 wherein specific binding of the pair inhibits absorption by the second fluorophore of light emitted by the first fluorophore.

34. The method of claim 33 wherein said ligand is Digoxin.

35. The method of claim 33 wherein said second member is receptor and said receptor is antibody to said ligand.

36. The method of claim 35 wherein said ligand is Digoxin.

37. The method of claim 33 wherein the first fluorophore is fluorescein and the second fluorophore is eosin.

38. The method of claim 37 wherein said member is receptor and said receptor is antibody to said ligand and said ligand is Digoxin.

39. The method of claim 29 wherein specific binding of the pair enhances absorption by the second fluorophore of light emitted by the first fluorophore.

40. The method of claim 39 wherein said ligand is Hepatitis B Surface Antigen, Immunoglobulin G, or Thyroxin.

41. The method of claim 39 wherein said second member is receptor and said receptor is antibody to said ligand.

42. The method of claim 41 wherein said ligand is Hepatitis B Surface Antigen, Immunoglobulin G, or Thyroxin.

43. The method of claim 39 wherein the first fluorophore is fluorescein and the second fluorophore is eosin.

44. The method of claim 43 wherein said member is receptor and said receptor is antibody to said ligand and said ligand is Hepatitis B Surface Antigen, Immunoglobulin G, of Thyroxin.

* * * * *

UNITED STATES PATENT AND TRADEMARK OFFICE
CERTIFICATE OF CORRECTION

PATENT NO. : 4,777,128

DATED : OCTOBER 11, 1988

INVENTOR(S) : ARNOLD S. LIPPA

It is certified that error appears in the above-identified patent and that said Letters Patent is hereby corrected as shown below:

Front Page, [57], line 3, delete "liquid" and substitute therefor -- ligand --;

Column 7, line 50, delete ",";

, line 59, delete "fluorsp-" and substitute therefor -- fluorop- --;

Column 8, line 32, delete "Imunoglobu-" and substitute therefor -- Immunoglobu- --;

, line 37, delete "of" and substitute therefor -- by --;

Column 10, line 21, delete "of" and substitute therefor -- or --.

Signed and Sealed this

Twentieth Day of February, 1990

*Attest:*

JEFFREY M. SAMUELS

*Attesting Officer*    *Acting Commissioner of Patents and Trademarks*